(12) United States Patent
Takahashi

(10) Patent No.: US 9,144,541 B2
(45) Date of Patent: *Sep. 29, 2015

(54) TITANIA FINE-PARTICLE COMPOSITE AND COMPOSITIONS CONTAINING THE TITANIA FINE-PARTICLE COMPOSITE

(71) Applicant: Pola Chemical Industries Inc., Shizuoka-shi, Shizuoka (JP)

(72) Inventor: Eiji Takahashi, Yokohama (JP)

(73) Assignee: POLA CHEMICAL INDUSTRIES INC., Shizuoka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/591,402

(22) Filed: Jan. 7, 2015

(65) Prior Publication Data

US 2015/0125501 A1 May 7, 2015

Related U.S. Application Data

(63) Continuation of application No. 12/989,145, filed as application No. PCT/JP2009/058368 on Apr. 28, 2009, now Pat. No. 8,945,520.

(30) Foreign Application Priority Data

May 2, 2008 (JP) ................. 2008-120069

(51) Int. Cl.
*A61K 8/29* (2006.01)
*A61Q 17/04* (2006.01)
*A61K 8/81* (2006.01)
*A61K 8/11* (2006.01)
*A61K 8/362* (2006.01)
*A61K 8/39* (2006.01)
*B82Y 30/00* (2011.01)
*C09C 1/36* (2006.01)
*A61K 8/02* (2006.01)
*A61K 8/34* (2006.01)
*A61Q 1/02* (2006.01)

(52) U.S. Cl.
CPC ............. *A61K 8/8147* (2013.01); *A61K 8/0241* (2013.01); *A61K 8/11* (2013.01); *A61K 8/29* (2013.01); *A61K 8/345* (2013.01); *A61K 8/362* (2013.01); *A61K 8/39* (2013.01); *A61K 8/8164* (2013.01); *A61Q 17/04* (2013.01); *B82Y 30/00* (2013.01); *C09C 1/3661* (2013.01); *C09C 1/3669* (2013.01); *C09C 1/3676* (2013.01); *C09C 1/3692* (2013.01); *A61K 2800/412* (2013.01); *A61Q 1/02* (2013.01); *C01P 2002/82* (2013.01); *C01P 2004/64* (2013.01); *C01P 2006/22* (2013.01)

(58) Field of Classification Search
None
See application file for complete search history.

(56) References Cited

U.S. PATENT DOCUMENTS

| | | | |
|---|---|---|---|
| 4,752,340 A | 6/1988 | Brand et al. | |
| 5,385,960 A | 1/1995 | Emmons et al. | |
| 5,698,205 A | 12/1997 | Bruckner et al. | |
| 6,416,748 B1 | 7/2002 | Candau et al. | |
| 6,420,437 B1 | 7/2002 | Mori et al. | |
| 6,576,051 B2 | 6/2003 | Bardman et al. | |
| 2005/0239921 A1 | 10/2005 | Birmingham et al. | |
| 2006/0264520 A1 | 11/2006 | Sonezaki et al. | |
| 2007/0105947 A1* | 5/2007 | Tada et al. | 514/456 |
| 2008/0305338 A1 | 12/2008 | Mizutani et al. | |
| 2010/0119829 A1 | 5/2010 | Karpov et al. | |

FOREIGN PATENT DOCUMENTS

| | | |
|---|---|---|
| AU | 727150 | 9/1997 |
| CA | 2623627 | 4/2007 |
| JP | 63-123815 | 5/1988 |

(Continued)

OTHER PUBLICATIONS

Chen et al., "Crosslinking of cotton cellulose with succinic acid in the presence of titanium dioxide nano-catalyst under UV irradiation", 2006, J Sol-Gel Sci Techn, 40: 31-38.
Decision on Grant dated May 11, 2012 to corresponding Russian patent application No. 2010149226/05(071065).
Inagaki et al., "Preparation of stable anatase-type TiO2 and its photocatalytic performance", 2001, International Journal of Inorganic Materials, 3: 809-811.
International Search Report dated Aug. 11, 2009 issued to international application No. PCT/JP2009/058368.
Office Action issued in corresponding Canadian Patent Application No. 2,722,795, on Jun. 14, 2013.

*Primary Examiner* — Robert A Wax
*Assistant Examiner* — Randeep Singh
(74) *Attorney, Agent, or Firm* — Knobbe, Martens, Olson & Bear, LLP

(57) ABSTRACT

Provided are a novel titania fine-particle composite which has high transparency, high stability, and high ultraviolet-absorbing power and excellent redispersibility, and skin-care external preparations which contain the titania fine-particle composite and exert high ultraviolet protective effect. The titania fine-particle composite can be produced by adding one or more selected from among carboxylic acids and carboxylic acid derivatives represented by general formula (1), and polymers containing the carboxylic acids or carboxylic acid derivatives as a constituent monomer to an aqueous acid dispersion of titania fine particles, and neutralizing the resulting dispersion with an alkali to form a titania fine-particle composite composed of titania fine particles functioning as cores and the carboxylic monomer or polymer deposited on the surface of the cores. In the titania fine-particle composite, titania fine particles functioning as cores have a high degree of crystallization and the intermolecular interaction between titania fine particles and the carboxylic monomer or polymer is strong. Therefore, the titania fine-particle composite can be uniformly dispersed in a dispersion medium to attain high transparency and high stability. Further, skin-care external preparations which exert high ultraviolet protective effect can be produced by adding the titania fine-particle composite.

3 Claims, No Drawings

(56) References Cited

FOREIGN PATENT DOCUMENTS

| | | |
|---|---|---|
| JP | 07-089722 | 4/1995 |
| JP | 11-278843 | 10/1999 |
| JP | 2001-029795 | 2/2001 |
| JP | 2001-207060 | 7/2001 |
| JP | 2003-096437 | 4/2003 |
| JP | 2004-203768 | 7/2004 |
| JP | 2005-232069 | 9/2005 |
| JP | 2006-160651 | 6/2006 |
| JP | 2007-291094 | 11/2007 |
| JP | 2009-149561 | 7/2009 |
| RU | 2 018 512 C1 | 8/1994 |
| RU | 2 162 443 C2 | 1/2001 |
| WO | WO 2007/057997 | 5/2007 |

\* cited by examiner

TITANIA FINE-PARTICLE COMPOSITE AND COMPOSITIONS CONTAINING THE TITANIA FINE-PARTICLE COMPOSITE

CROSS-REFERENCE TO RELATED APPLICATIONS

This application is a continuation of U.S. application Ser. No. 12/989,145, filed Oct. 22, 2010 which is the U.S. National Phase under 35 U.S.C. §371 of International Application PCT/JP2009/058368, filed Apr. 28, 2009, which was published in a non-English language, which claims priority to JP Application No. 2008-120069, filed May 2, 2008.

TECHNICAL FIELD

The present invention relates to a titania fine-particle composite that is useful as an ultraviolet protection agent, a method of producing the composite, and compositions containing the composite.

BACKGROUND ART

It is known that ultraviolet A (UVA) in a wavelength region of 320 to 400 nm and ultraviolet B (UVB) in a wavelength region of 290 to 320 nm reach down to the ground without being sufficiently absorbed and scattered by the ozone layer, and cause various negative effects on skin. For example, it is known that UVB induces inflammation and accelerates skin aging and that UVA accelerates melanin production and causes blotches, freckles, and so on.

Cosmetics for preventing such negative effects on skin have been developed and examined in various ways. For example, there has been made an attempt to prevent skin from excessively getting exposed to ultraviolet rays through the use of a compound having an aromatic ring such as a benzene ring, i.e., the so-called UV absorbing agent (see Patent Document 1 and 2, for example).

However, as many of the UV absorbing agents used in these documents are oils, the agents have low solubility in water, and thus their forms as cosmetics are sometimes limited. When these UV absorbing agents are used as cosmetics, a refreshing tactile sensation is hardly obtained. Because of this, there has been a limit to use these UV absorbing agents as ultraviolet protection cosmetics frequently used in summer.

Meanwhile, there has been made a report on an attempt to prevent skin from excessively getting exposed to ultraviolet rays by using inorganic fine particles such as zinc oxide fine particles or titanium oxide fine particles (see Patent Documents 3 and 4, for example). It is known that zinc oxide, titanium oxide, and the like have great UV protective effects. In particular, it is known that titanium oxide has a high level of UVB shielding ability and zinc oxide has a high level of UVA shielding ability.

However, making titanium oxide fine particles or zinc oxide fine particles into an uniform dispersion in an aqueous solution tends to be hindered because of their surface activities. Accordingly, adding titanium oxide or zinc oxide to a cosmetic base leads to nonuniform dispersion. As a result, the cosmetic that has become a cloudy solution is applied to a face or a body, which causes problems including the face or the body turns whitish and the UV protective effect of the cosmetic is diminished. Further, there has been a problem in that titanium oxide or zinc oxide affects other compounding ingredients, such as a thickening agent, in a cosmetic and the function of the cosmetic deteriorates, for example.

In order to disperse uniformly titanium oxide or zinc oxide in an aqueous solution, a method of making titanium oxide or zinc oxide into a superfine particles and a method of adding a surface active agent to the aqueous solution have been worked out. An example of the method of adding of a surface active agent includes a method of preparing a neutral titania sol by compounding a water-soluble high-molecular compound (polyvinyl alcohol or the like) as a dispersion stabilizing agent into an aqueous acid solution containing titania fine particles and then compounding an alkaline solution as a neutralizing agent into the resultant solution (Patent Document 5); however, when a cosmetic additive agent was added, maintaining the stability of the neutral titania sol was difficult.

Moreover, to uniformly disperse titanium oxide or zinc oxide in a solution, there has also been made a report of treating the surfaces of the inorganic fine particles with a silicone-based copolymer, a particular phosphate ester, or the like (see Patent Documents 6 and 7, for example); however, the treatment is insufficient in effect.

The inventors of the present invention have produced metal oxide fine-particle composites by dissolving a particular short-chain fatty acid or polymer and so on and a metal salt in a water-soluble organic solvent or a mixed solution of water and a water-soluble organic solvent and then neutralizing the metal salt or reducing the metals in the metal salt (Patent Document 8). Among such metal oxide fine particle composites, zinc oxide fine particles can be dispersed uniformly in the aqueous solution and have both transparency and ultraviolet absorbency. On the other hand, in the case of the titanium oxide fine-particle composite, the dispersibility in an aqueous solution is not enough so that both transparency and ultraviolet absorbency could have not been sufficiently attained. Further, there are also problems that the titanium oxide fine particles cannot be redispersed when once the particles aggregate because of the instability in the composite state and the dispersion of the composite has high viscosity.

In view of such circumstances, it is desired that a titania fine-particle composite, which is excellent in transparency and ultraviolet-absorbing effect and is stable in a composite state, be developed because the composite has broad utility.

CITATION LIST

Patent Document

[Patent Document 1] JP 2001-207060 A
[Patent Document 2] JP 2006-160651 A
[Patent Document 3] JP 2004-203768 A
[Patent Document 4] JP 2003-096437 A
[Patent Document 5] JP 63-123815 A
[Patent Document 6] JP 2007-291094 A
[Patent Document 7] JP 2005-232069 A
[Patent Document 8] WO 2007/057997 A1

SUMMARY OF INVENTION

Technical Problem

The present invention has been accomplished under such circumstances, an object of the present is to provide a novel titania fine-particle composite which is uniformly dispersed in a dispersion medium and secures, therefore, high transparency, high stability, and high ultraviolet-absorbing power. Another object of the present invention is to provide a titania fine-particle composite, which maintains, even when the titania fine-particle composite is added to a cosmetic along with other compositions, the state of the composite of being uniformly dispersed and has high practicability as a cosmetic composition.

Solution to Problem

The inventors of the present invention have conducted extensive studies in order to provide a novel titania fine-particle composite with high practicability. As a result, the inventors have found that a titania fine-particle composite, comprising one or more selected from a carboxylic acid and a carboxylic acid derivative represented by the following general formula (1), and a polymer containing, as constituent monomers, the carboxylic acid and/or the carboxylic acid derivative (hereinafter, referred to as "carboxylic acid monomer or polymer, or the like") deposited on the surfaces of titania fine particles, in which the half-value width of the peak of maximum diffraction intensity attributed to titania is 2.0° or less in X-ray powder diffraction analysis, is uniformly dispersed in a dispersion medium.

Moreover, the inventors have found that the titania fine-particle composite can be obtained by adding the carboxylic acid monomer or polymer, or the like to an aqueous acid dispersion containing the titania fine particles and then neutralizing the aqueous dispersion. Thus, the present invention has been accomplished.

That is, the present invention is represented as follows:

Advantageous Effects of Invention

In the titania fine-particle composite of the present invention, the aggregation among the titania fine-particle composites hardly occurs, and thus the composites can be dispersed uniformly in a dispersion medium. Therefore, the composition containing the titania fine-particle composite of the present invention has high transparency, high stability, and high ultraviolet-absorbing power.

In the titania fine-particle composite of the present invention, even once the particles have been filtered out from a dispersion medium, the particles can be redispersed uniformly in the dispersion medium.

Moreover, the neutral dispersion containing the titania fine-particle composite of the present invention has a lower viscosity than neutral dispersions containing conventional titania fine-particle composites, and thus it is easy to process the composite of the present invention into a cosmetic and so on. Further, the neutral dispersion containing the titania fine-particle composite of the present invention can also be compounded into a cosmetic at a high concentration. Furthermore, even when other components are added along with the composite of the present invention at the time of the preparation of a cosmetic, a uniform dispersion state can be maintained.

As such, the titania fine-particle composite of the present invention is excellent in practicability and general-purpose properties.

DESCRIPTION OF EMBODIMENTS

A titania fine-particle composite of the present invention is a titania fine-particle composite, including compounding titania fine particles combined with one or more selected from among carboxylic acids and a carboxylic acid derivatives represented by the general formula (1), and polymers containing, as constituent monomers, the carboxylic acid and/or the carboxylic acid derivative, in which the half-value width of the peak of maximum diffraction intensity attributed to titania crystals is 2.0° or less in X-ray powder diffraction analysis.

When X-ray powder diffraction analysis is performed on the titania fine-particle composite of the present invention, the half-value width of the peak of maximum diffraction intensity attributed to the titania crystals in the analysis chart is 2.0° or less.

In the present invention, the term "half-value width" is defined as a value found by performing X-ray powder diffraction analysis under the following conditions. A dry sample of the titania fine-particle composite is pulverized into a measurement powder. An X-ray diffraction (XRD) measurement is performed on the measurement powder by using an X-ray diffraction apparatus (available from Spectris Co., Ltd., Tradename: PANalytical X'Pert PROMPD). The measurement is performed by using a CuK$\alpha$ ray as an X-ray source at a scanning angle $2\theta=5°$ to $70°$ under the conditions that the tube voltage is 45 kV and the tube current is 40 mA. Then the half-value width of the peak of maximum diffraction intensity is found from the diffraction chart made based on the measurement.

It should be noted that the peak of the maximum diffraction intensity attributed to the titania crystals forms at a scanning angle $2\theta=27.5°$ in the case where rutile crystals are formed, and forms at a scanning angle $2\theta=25.5°$ in the case where anatase crystals are formed.

The peak intensity in the X-ray diffraction analysis chart represents an abundance ratio on crystalline planes of the powder. The term "half-value width" refers to the difference between two values of the abscissa axis (a width of a mountain) on the ordinate axis of the mountain-shaped curve at a location representing a half of a value of the ordinate axis of the peak, which is mountain-shaped. In general, the half-value width of the peak of maximum diffraction intensity represents the crystallinity indices of the powder. For example, the case where half-value width of a peak corresponding to a (101) plane is small, that is, the case where a peak is formed clearly means that the crystallinity index at the (101) plane is high, and thus it can be said that crystallinity is heightened and a stable crystalline state is, therefore, brought about. On the other hand, the case where the half-value width of a peak corresponding to the (101) plane is large, that is, the case where the peak is gentle means that crystallization at the (101) plane does not proceed, and thus a near-amorphous state is brought about. In the titania fine-particle composite of the present invention, the case where the half-value width is 2.0° or less means a state in which the crystallinity of the titania fine particles as the core portions of the titania fine-particle composite is heightened.

When the half-value width is in the foregoing range, the titania fine-particle composite is dispersed uniformly in the dispersion medium, whereby transparency and ultraviolet absorbency can be realized. Further, as is clear from a comparison of Example 1 and Comparative Example 4 described later, a dispersion containing such titania fine-particle composite at a high concentration has a considerably lower viscosity than a dispersion containing a conventional titania fine-particle composite at the same concentration. This is probably because the intermolecular interactions of the titania fine particles and the carboxylic acid monomer or polymer, or the like become strong.

The titania fine-particle composite with the half-value width of 2.0° or less can be produced by using a method described below.

The titania fine particles as the core portions of the titania fine-particle composite of the present invention are crystallized titanium oxide. As the form of the crystal, any one of the rutile-type crystal form and the anatase-type crystal form may be given; both the forms may be mixed together; or part of the particles may be uncrystallized titania fine particles. Of these forms preferred is the rutile-type crystal form that has low surface activity and can be expected to have ultraviolet absorbing ability.

Moreover, the titania fine particles as the core portions of the titania fine-particle composite of the present invention may be coated with one or more kinds of hydrated oxides of silicon, aluminium, zirconium, and the like. By the surface coating on the fine particles, the surface activity of the particles can be suppressed. However, it should be noted that in the case where particle diameters are increased due to the surface treatment, reduced ultraviolet absorption efficiency is sometimes brought.

In the general formula (1), R represents a hydrogen atom, a $C_1$ to $C_{15}$ alkyl group or a $C_1$ to $C_{15}$ alkenyl group in which hydrogen atoms may be substituted with a carboxyl group or a hydroxy group. When hydrogen atoms of the alkyl group or the alkenyl group are substituted with a carboxyl group, the carbon number of the alkyl group or the alkenyl group is defined as a carbon number brought in the case where it is hypothesized that such substitutions were not made. X represents a hydrogen atom, an alkali metal, or a polyoxyalkylene group with an addition mole number of 1 to 12.

R preferably represents a $C_1$ to $C_8$ alkyl group or a $C_1$ to $C_8$ alkenyl group in which hydrogen atoms may be substituted with a carboxyl group or a hydroxy group. In the case where R represents an unsubstituted alkyl group, examples of the carboxylic acid represented by the general formula (1) include acetic acid, propionic acid, and caproic acid. In the case where R represents an unsubstituted alkenyl group, examples of the carboxylic acid represented by the general formula (1) include acrylic acid and methacrylic acid. In the case where R represents an alkyl group in which hydrogen atoms are substituted with a carboxyl group or a hydroxy group, suitable examples of the carboxylic acid represented by the general formula (1) include oxalic acid, malonic acid, tartaric acid, succinic acid, and citric acid. That is, the carboxylic acid represented by the general formula (1) maybe a monocarboxylic acid, or a polycarboxylic acid such as a dicarboxylic acid or a tricarboxylic acid; a carboxylic acid having 10 or less carbon atoms is preferred.

In the case where X represents an alkali metal, examples of the metal include potassium, sodium, and lithium. In the case where X represents a polyoxyalkylene group, its average addition mole number is preferably 1 to 12, more preferably 2 to 8. Suitable examples of the polyoxyalkylene group include a polyoxyethylene group and a polyoxypropylene group.

Further, as the carboxylic acid derivative represented by the general formula (1), particularly preferred is an alkali metal salt of a polycarboxylic acid such as the monocarboxylic, dicarboxylic, or tricarboxylic acid having 10 or less carbon atoms or a carboxylic acid derivative in which polyoxyalkylene is added to part of the carboxyl groups or the hydroxyl groups. In particular, in the case where the carboxylic acid is a polycarboxylic acid, a form in which part of the acid is converted to a salt is preferred. Examples of such alkali metal salt include sodium acetate, potassium propionate, sodium acrylate, triethylamine methacrylate, sodium caprate, lithium oxalate, potassium malonate, sodium succinate, potassium citrate, and sodium tartrate. In addition, examples of the polyoxyethylene adduct include polyoxyethylene acrylate and polyoxyethylene methacrylate.

Examples of the polymer containing, as constituent monomers, the carboxylic acid and/or the carboxylic acid derivative represented by the general formula (1) include a polymer containing methacrylic acid or acrylic acid, or a polyoxyethylene adduct, a metal salt, or an alkali metal salt thereof as constituent monomers in which alkenyl groups as side chains of a carboxylic acid have become polymeric groups. The degrees of polymerization of these polymers are preferably 1000 or less.

Suitable examples of the polymer include a homopolymer produced by polymerizing the constituent monomers and a copolymer of the constituent monomers and monomers of vinyl acetate, vinyl alcohol, styrene, or monomers other than the compounds represented by the general formula (1) such as an alkyl(meth) acrylate including methyl methacrylate.

Specific examples of the polymer include polyacrylic acid, sodium polyacrylate, triethanolamine polyacrylate, sodium polymethacrylate, triethylamine polymethacrylate, and a polyoxyethylene acrylic polymer or a polyoxyethylene methacrylic polymer having an addition mole number of oxyethylene of 23 or less.

The titania fine-particle composite of the present invention, including titania particles combined with a polymer containing the carboxylic acid and/or the carboxylic acid derivative represented by the general formula (1) as constituent monomers can be dispersed in a neutral aqueous solution. On the other hand, the titania fine-particle composite of the present invention, including titania particles combined with the carboxylic acid and the carboxylic acid derivative represented by the general formula (1) can be dispersed in a hydrophobic solvent.

In the titania fine-particle composite of the present invention, the absorption peak of a carbonyl group in an infrared absorption spectrum measured by using a KBr tablet method preferably appears in the wavelength region of 1535 to 1545 $cm^{-1}$.

In the present invention, an infrared absorption spectrum is defined as a spectrum that can be obtained by conducting measurement under the following conditions. After a neutral aqueous dispersion of the titania fine-particle composite of the present invention is dried at 105° C., the dried mixture is pulverized into a measurement powder. The measurement powder is shaped into a KBr tablet, following which a spectrum of an infrared ray absorbed by the tablet is measured by using a Fourier transform infrared spectrophotometer (from Shimadzu Corp., Product Code: FTIR-8300).

In the case where the absorption peak is in the foregoing region, the titania fine-particle composite is uniformly dispersed in the dispersion medium, and thus transparency and ultraviolet absorbency can be attained. Further, as is clear from the comparison of Example 1 and Comparative Example 4 described later, a dispersion containing such titania fine-particle composite at a high concentration has a considerably lower viscosity than a dispersion containing a conventional fine-particle composite at the same concentration has.

In general, the absorption peak attributed to the carbonyl groups of the carboxylic acid monomer or polymer, or the like exists in a wavelength region that is longer than the wavelength region of 1535 to 1545 $cm^{-1}$; for example, in sodium polyacrylate, the absorption peak exists in the wavelength region of 1558 to 1560 $cm^{-1}$. As shown in Example 1, however, in the titania fine-particle composite of the present invention, it can be considered that as the intermolecular interactions of the titania particles and the carboxylic acid monomer or polymer, or the like are strong, part of the carbonyl groups of the carboxylic acid monomer or polymer, or the like is constrained at the surfaces of the titania fine particles and therefore the absorption peak attributed to the carbonyl groups also appears in the wavelength region of 1535 to 1545 cm$^{-1}$. On the other hand, as shown in Comparative Example 4 described later, in the conventional titania fine-particle composite described in Patent Literature 8, the absorption peak attributed to each carbonyl group does not appear in the wavelength region of 1535 to 1545 cm$^{-1}$, and thus such conventional composite can be distinguished from the titania fine-particle composite of the present invention.

The titania fine-particle composite in which the absorption peak appears in the region of 1535 to 1545 cm$^{-1}$ can be produced by using a method described later.

In the titania fine-particle composite of the present invention, the weight ratio of the titania fine particles to the carboxylic acid monomer or polymer, or the like is preferably 60% or higher. The weight ratio is preferably 60 to 99%, more preferably 85 to 99%. However, when the particle diameters of the titania fine-particle composite increase, the composite tends to uniformly disperse in the dispersion medium less easily, and therefore it cannot be said unconditionally that which weight ratio is preferred.

The titania fine-particle composite of the present invention is high in degree of the intermolecular interactions of the titania fine particles and the carboxylic acid monomer or polymer, or the like, and therefore, even when the carboxylic acid monomer or polymer, or the like to be combined to the titania particles has low weight ratio, the composite effect is sufficiently achieved, and the fine particles can be, therefore, uniformly dispersed in the dispersion medium.

In the case where the titania fine-particle composite of the present invention is used as an ultraviolet absorbing agent, the diameters of the titania particles are preferably 0.002 to 5 μm, particularly preferably 1 μm or less. Because, in the titania fine-particle composite of the present invention, the amount of the carboxylic acid monomer or polymer, or the like to be combined may be small as described above, the diameters of the titania fine particles are decreased, and the surface area of the whole titania fine particles can be increased by their uniform dispersion into the dispersion medium; therefore the titania fine-particle composite is suited for an ultraviolet absorbing agent.

The shape of the particles of the titania fine-particle composite can be observed with a scanning electron microscope, and the maximum diameter thereof can also be measured by attaching a scale thereto.

The titania fine-particle composite of the present invention can be produced by using the following method.

To an aqueous acid dispersion of titania fine particles, one or more selected from a carboxylic acid and a carboxylic acid derivative represented by the general formula (1), and a polymer containing, as constituent monomers, the carboxylic acid and/or the carboxylic acid derivative are gradually added under stirring to give a mixed solution. Thereafter, to sufficiently make the system uniform, the mixed solution may be allowed to standstill for about 1 min to 1 hr for aging. Then, an alkali such as a sodium hydroxide is added to the mixed solution under stirring until the solution reaches a neutral pH region (a pH of 5 to 7.5) to give a neutral solution. After the neutralization, the neutral solution may be allowed to stand still for about 1 min to 1 hr to sufficiently carry out the combination reaction.

All of the above-mentioned steps can be executed at ambient temperature (at a temperature of 15° C. to 30° C.)

It should be noted that the above-mentioned alkali addition starts the combination reaction between the titania fine particles and the carboxylic acid monomer or polymer, or the like. That is, anions, by which the titania fine particles are dispersed in water, leave the titania fine particles by the alkali neutralization (in the case where the acid in the dispersion medium is a hydrochloric acid, chlorine ions leave, and in the case where the acid in the dispersion medium is a nitric acid, nitrate ions leave, for example); instead of the anions, the carboxylic acid monomer or polymer, or the like is combined to the titania fine particles by their intermolecular interactions.

Whereas the titanium fine-particle composite of the present invention is produced by executing the foregoing steps, the resulting neutral solution can be further processed into a skin-care external preparation by filtering the neutral solution, washing the filtered residue with water, and then removing the salt to provide a wet cake. Then the wet cake is redispersed in a dispersion medium to prepare a slurry; the slurry state is preferred in the case of handling the composite as a material for a skin-care external preparation. It should be noted that the redispersion may be done with ultrasound; in addition, before the redispersion, the cake may be put into a mill (a ball mill, a sand grinding mill, or the like).

In the following, the producing method is described in detail.

To uniformly disperse the titania fine particles in the aqueous acid dispersion, the concentration of the particles is preferably 10 wt % or less, more preferably 5 wt % or less, and still more preferably 2.5 wt % or less.

In the dispersion medium (the peptizing agent) in the aqueous acid dispersion of the titania fine particles, as the acid added to water, hydrochloric acid, nitric acid, sulfuric acid, phosphoric acid, or the like can be used; hydrochloric acid or nitric acid is particularly preferred. Further, the pH of the aqueous acid dispersion of the titania fine particles is preferably in the range of 1 to 2.

As the alkali added at the time of the neutralization, sodium hydroxide, potassium hydroxide, or the like can be used; sodium hydroxide is particularly preferred.

Although the carboxylic acid monomer or polymer, or the like maybe added directly to the aqueous acid dispersion of the titania fine particles, it is preferred that the carboxylic acid monomer or polymer, or the like be previously dissolved to a solution in order to achieve a uniform combination. The concentration of the carboxylic acid monomer or polymer, or the like in the solution is preferably 0.01 to 1 wt %. As the solvent, a mixed solvent of an alcohol and water is suitable; as the alcohol, ethanol, isopropyl alcohol, methanol, or 1,3-butylene glycol can be used.

It is preferred that the titania fine particles and the carboxylic acid monomer or polymer, or the like be compounded in a weight ratio of 5:1 to 14:1. The case where the weight ratio of the carboxylic acid monomer or polymer, or the like is higher than the above-mentioned ratio is not preferred because the titania fine-particle composite becomes sticky.

The titania fine particles used for the method of producing the titania fine-particle composite of the present invention can be obtained by using any of various methods known per se. Examples of such producing methods include a method involving heating and aging hydrated titanium oxide prepared by neutralizing a water-soluble titanium salt such as titanium tetrachloride or titanium oxysulfate with an alkali, a method involving heating and aging hydrated titanium oxide prepared by hydrolyzing a titanium alkoxide, and a method involving heating and aging titanium hydroxide prepared by heating and hydrolyzing titanium oxysulfate solution. In addition, there also is a producing method in which instead of heating and aging, tin oxide as a transferring agent is added to titanium hydroxide and then the mixture is peptized with an acid.

Further, the titania fine particles coated with one or more kinds of hydrated oxides of silicon, aluminium, zirconium, and the like can be obtained by using a method known per se. For example, such particles can be obtained by mixing under wet conditions a titanium fine particle-dispersed product prepared in advance into a gel formed by neutralization of sodium silicate and depositing the particles. Further, the particles can also be produced by treating a soluble salt of a metal such as aluminium with an acid under the presence of a titania fine particle-dispersed product and depositing the particles in the form of an insoluble metal hydroxide such as aluminium hydroxide.

In the cases where it is desired that the titania fine particles have transparency and where the particles are used for ultraviolet absorption, sterilization, and so on, it is preferred that the particle diameters be small; the maximum diameter of the titania fine particles is preferably about 0.001 to 0.1 μm.

Compositions containing the titania fine-particle composite of the present invention have low viscosity in a neutral aqueous dispersion so that have high fluidity. This is because the titania fine-particle composite of the present invention disperses in the neutral aqueous dispersion uniformly and therefore aggregation of the titania fine particles hardly occurs.

As the viscosity thereof is low, the composite is easy to treat in producing cosmetics, and allows cosmetics to exhibit a refreshing tactile sensation.

As the titania fine-particle composite of the present invention is high in the degree of the intermolecular interactions between the titania fine particles as the core portions thereof and the carboxylic acid monomer or polymer, or the like, the interactions among the components of the monomer, the polymer, or the like become relatively weak; thus the titania fine-particle composite can be dispersed uniformly in the neutral aqueous dispersion without aggregating. Because of this, the composite has a high degree of visible light transmission and is, therefore, transparent; moreover, as the surface area of the whole titania fine particles is increased, the composite of the present invention has a high degree of ultraviolet shield factor.

Due to these properties, cosmetics containing the titania fine-particle composite of the present invention are allowed to have high transparency, and has an effect of causing a face or a body to become whitish less easily to which any of the cosmetics is applied. Further, the titania fine-particle composite of the present invention, having such high degree of ultraviolet shield factor, is suitable for the production of cosmetics with high ultraviolet-absorbing power.

The titania fine-particle composite of the present invention can be used as a skin-care external preparation for cosmetics; suitable examples of cosmetics containing such a preparation include: ultraviolet protection cosmetics such as sun care milk, sun care powder, and sun block; makeup cosmetics such as under makeup, foundation, control color, and pressed powder; and, in particular, summer makeup cosmetics.

Regarding an application form, the composite of the present invention is applicable to any of a two-layer dispersion lotion, an emulsifier, a powder, an oil, and so on. As the titania fine-particle composite of the present invention can also be dispersed uniformly in aqueous media, the form of an aqueous carrier-containing two-layer dispersion lotion or an emulsifier is particularly preferred.

In the case where the titania fine-particle composite of the present invention is compounded with a composition such as a skin-care external preparation, the content of the composite in the whole composition thus prepared is preferably 0.5 to 50 wt %, more preferably 1.0 to 30 wt %.

The skin agent for external use of the present invention may contain, apart from the above-mentioned ingredients, an arbitrary ingredient generally used for a skin agent for external use. Preferred examples of the arbitrary ingredient include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as oleyl alcohol, cetyl alcohol, stearyl alcohol, isostearyl alcohol, behenyl alcohol, octyldodecanol, myristyl alcohol, and cetostearyl alcohol; synthetic ester oils such as cetyl isoctanoate, isopropyl myristate, hexyldecyl isostearate, diisopropyl adipate, diethyl sebacate, diisopropyl sebacate, di-2-ethylhexyl sebacate, cetyl lactate, diisostearylmalate, ethylene glycol di-2-ethyl hexanoate, neopentyl glycol dicaprate, di-2-heptyl undecanoic acid glyceride, tri-2-ethylhexanoic acid glyceride, trimethylolpropane tri-2-ethylhexanoate, trimethylolpropane triisostearate, and pentane erythrite tetra-2-ethylhexanoate; silicone oils such as silicones including dimethylpolysiloxane, cyclodimethylpolysiloxane and the like, amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium lauryl sulfate, triethanolamine alkyl sulfate ether, and sodium polyoxyethylene lauryl phosphate; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazoliniumhydroxide-1-carboxyethyloxy-2-sodium salt), betaine-based surfactants (such as alkyl betaine, amide betaine, and sulfo betaine), and acylmethyl taurine; nonionic surfactants such as sorbitan fatty acid esters (such as sorbitan monostearate, sorbitan monolaurate, and sorbitan sesquioleate), glycerin fatty acids (such as glycerin monostearate), propyleneglycol fatty acid esters (such as propyleneglycol monostearate), cured castor oil derivatives, glycerol alkyl ether, POE sorbitan fatty acid esters (such as POE sorbitan monooleate, polyoxyethylene sorbitan monostearate, and polyoxyethylene sorbitan monolaurate), POE sorbitol fatty acid esters (such as POE-sorbitol monolaurate), POE glycerol fatty acid esters (such as POE-glyceryl monoisostearate), POE fatty acid esters (such as polyethyleneglycol monooleate and POE distearate), POE alkyl ethers (such as POE lauryl ether, POE oleyl ether, and POE 2-octyldodecyl ether), POE alkyl phenyl ethers (such as POE octylphenyl ether and POE nonylphenyl ether), pluronic types, POE/POP alkyl ethers (such as POE/POP 2-decyltetradecyl ether), tetronic types, POE castor oil/cured castor oil derivatives (such as POE castor oil and POE cured castor oil), sucrose fatty acid ester, and alkyl glycoside; polyhydric alcohols such as polyethyleneglycol, glycerin, 1,3-butylene glycol, erythritol, sorbitol, xylitol, maltitol, gluconolactone, propylene glycol, dipropylene glycol, diglycerin, isoprene glycol, 1,2-pentanediol, 2,4-hexanediol, 1,2-hexanediol, 1,2-octanediol, polypropylene glycol, and 2-ethyl-1,3-hexanediol; moisturizing ingredients such as sodium pyrrolidone carboxylate, lactic acid, and sodium lactate; pH adjusters such as phosphoric acid and citric acid; powders such as mica, talc, kaolin, synthetic mica, and barium sulfate, whose surfaces may be treated; inorganic pigments such as colcothar, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic powders such as a polyethylene powder, polymethyl methacrylate, a nylon powder, and an organopolysiloxane elastomer; ultraviolet absorbents such as 2-(2'-hydroxy-5'-t-octylphenyl)benzotriazole and 4-methoxy-4'-t-butyldibenzoylmethane; lower alcohols such as ethanol and isopropanol; vitamins such as vitamin A and derivatives thereof, vitamin Bs such as vitamin $B_6$ hydrochloride, vitamin $B_6$ tripalmitate, vitamin $B_6$ dioctanoate, vitamin $B_2$ and derivatives thereof, vitamin $B_{12}$, and vitamin $B_{15}$ and derivatives thereof, vitamin Es such as α-tocopherol, β-tocopherol, γ-tocopherol, and vitamin E acetate, vitamin Ds, vitamin H, pantothenic acid, pantethine, and pyrroloquinoline quinone; and solvents such as benzyl alcohol, triacetin, crotamiton, carbonic diesters such as prolene carbonate, and ethylene glycol salicylate. In addition, as other ultraviolet absorbents, there also may be included a p-aminobenzoate-based ultraviolet absorbent, an anthranilate-based ultraviolet absorbent, a salicylate-based ultraviolet absorbent, a cinnamate-based ultraviolet absorbent, a benzophenone-based ultraviolet absorbent, and a sugar-based ultraviolet absorbent.

EXAMPLES

Hereinafter, the present invention is described in more detail by way of examples. However, the present invention is not limited to those examples.

<Preparation of Titania Fine-particle Composite>

Example 1

(a) Aqueous Acid Dispersion of Titania Fine Particles

A hydrated titanium oxide, which had been given by using a method known per se, i.e., by hydrolyzing titanium oxysulfide, was treated with an alkali, and then heated and aged in hydrochloric acid to give an aqueous acid dispersion of titania fine particles. The titania fine particles in the resulting aqueous acid dispersion had a rutile-type crystal structure, and had an average particle diameter of 0.01 μm. The concentration of the aqueous acid dispersion was adjusted with pure water to 100 g/L in terms of $TiO_2$, and 1 L of the aqueous acid dispersion of the titania fine particles was measured out.

(b) Combination Treatment Using Polyacrylic Acid

The aqueous acid dispersion of the titania fine particles given in the step (a) was diluted with pure water to give an aqueous titania fine-particle dispersion (5 L) with a $TiO_2$ concentration of 20 g/L (Solution A). Polyacrylic acid (20 g) (from Wako Pure Chemical Industries Ltd., molecular weight: 5000, polymerization degree: ca 50) was dissolved in pure water (8 L) to give a solution (Solution B). Solution A was gradually added to Solution B under stirring at ambient temperature, following which the resultant was aged for 1 hr. Then, the pH of the resultant was adjusted to 5 with an aqueous 2N sodium hydroxide solution, and the resulting solution was aged for 1 hr and filtered, after which the mixture filtered off was washed with pure water to give a wet cake. The wet cake was repulped in pure water, following which the repulped cake was dispersed with ultrasound to give a neutral aqueous dispersion of the titania fine-particle composite of the present invention (solid content concentration: 25%, pH: 7.5) (Sample A).

In titania fine-particle composite Sample A, the content of polyacrylic acid was 0.07 part by weight with respect to 1 part by weight of $TiO_2$, and the ratio of the titania fine particles in the titania fine-particle composite was 93.5 wt %.

When the redispersed aqueous solution of the titania fine-particle composite prepared by using the above-mentioned method was boiled and then filtered, almost no carboxylic acid monomer or polymer, or the like was found in the filtrate. Further, as the titania fine-particle composite is dispersed uniformly in the dispersion, it can be said that the titania fine-particle composite has high hydrophilicity as compared with the titania fine particles before the combination; therefore it is presumed that the carboxylic acid monomer or polymer, or the like is combined to the surfaces of the titania fine particles with strong interactions.

Example 2

The same treatment as that of Example 1 was carried out except that sodium polyacrylate (20 g) (from Wako Pure Chemical Industries Ltd., molecular weight: 5000, polymerization degree: ca 50) was used instead of the polyacrylic acid, giving a neutral aqueous dispersion of a titania fine-particle composite (Sample B) as the titania fine-particle composite of the present invention.

In Sample B, the ratio of the titania fine particles in the titania fine-particle composite was 96.0 wt %.

Example 3

The same treatment as that of Example 1 was carried out except that polymethacrylic acid (20 g) (from Wako Pure Chemical Industries Ltd., molecular weight: 100,000, polymerization degree: ca 1000) was used instead of the polyacrylic acid, giving a neutral aqueous dispersion of a titania fine-particle composite (Sample C) as the titania fine-particle composite of the present invention.

In Sample C, the ratio of the titania fine particles in the titania fine-particle composite was 92.0 wt %.

Example 4

The same treatment as that of Example 1 was carried out except that poly(acrylic acid/maleic acid) (20 g) (from NIPPON SHOKUBAI CO., LTD., molecular weight: 5000, polymerization degree: ca 50) was used instead of the polyacrylic acid, giving a neutral aqueous dispersion of a titania fine-particle composite (Sample D) as the titania fine-particle composite of the present invention.

In Sample D, the ratio of the titania fine particles in the titania fine-particle composite was 93.0 wt %.

Example 5

(C) Silica Coating Treatment on Titania Fine Particles

Silica coating treatment was performed on titania fine particles by using a method known per se. That is, the aqueous acid dispersion of the titania fine particles given in the step (a) of Example 1 was diluted with pure water to 20 g/L, and 5 L of the dilution was measured out (100 g in terms of $TiO_2$). Thereafter, the dispersion was heated to 70° C., and then an aqueous sodium silicate solution (170 mL) with a concentration of 400 g/L in terms of $SiO_2$ (12% in terms of $SiO_2$ with respect to the titania fine particles) was added thereto along with 20% sulfuric acid, following which the resultant was aged for 30 min. Then, the pH of the resultant was adjusted to 9.0 or higher with a 10% aqueous sodium hydroxide solution, and further adjusted to 3 with a 1% aqueous sulfuric acid solution, after which the dispersion was filtered, and the filtered residue was washed with pure water to give a wet cake. The wet cake was repulped in pure water, and dispersed with ultrasound, giving silica-coated titania fine particles A. In Sample A, the surfaces of the titania fine particles were coated with silica, and the content of the silica in terms of $SiO_2$ was 0.05 part by weight with respect to 1 part by weight of $TiO_2$.

(d) Combination Treatment Using Polyacrylic Acid

The same treatment as that of Example 1 was carried out except that the silica-coated titania fine particles A given in the step (c) were used instead of the aqueous acid dispersion of the titania fine particles, giving a neutral aqueous dispersion of a silica-coated titania fine-particle composite (Sample E) as the titania fine-particle composite of the present invention.

In Sample E, the ratio of the titania fine particles in the titania fine-particle composite was 93.0 wt %.

Example 6

The same treatment as that of Example 5 was carried out except that polymethacrylic acid (20 g) (from Wako Pure Chemical Industries Ltd., molecular weight: 100,000, polymerization degree: ca 1000) was used instead of the polyacrylic acid, giving a neutral aqueous dispersion of a silica-coated titania fine-particle composite (Sample F) as the titania fine-particle composite of the present invention.

In Sample F, the ratio of the titania fine particles in the titania fine-particle composite was 91.5 wt %.

Example 7

(e) Silica Coating Treatment and Alumina Coating Treatment on Titania Fine Particles The pH of the aqueous acid dispersion of the titania fine particles (1 L: 100 g in terms of $TiO_2$) given in the step (a) of Example 1 was adjusted to 9.0 or higher with sodium hydroxide. Thereafter, a 400 g/L aqueous sodium silicate solution (30 mL) (12% in terms of $SiO_2$ with respect to the titania fine particles) was added thereto, and the mixture was heated to 90° C. and then neutralized with sulfuric acid over 200 min so as to have a pH of 7.

To the aqueous suspension, polyaluminium chloride (80 g) (8% in terms of $Al_2O_3$ with respect to the titania fine particles) was added. After the addition, the suspension was neutralized with sodium hydroxide so as to have a pH of 5.0, and then the neutralized suspension was aged for 60 min to give silica-alumina-coated titania fine particles B. In the silica-alumina-coated titania fine particles B, the surfaces of the titania fine particles were coated with silica, and the ratio of the silica in terms of $SiO_2$ was 0.12 part by weight with respect to 1 part by weight of $TiO_2$. Further, each silica layer was coated with alumina, and the ratio of the alumina in terms of $Al_2O_3$ was 0.08 part by weight with respect to 1 part by weight of $TiO_2$.

(f) Combination Treatment Using Polyacrylic Acid

The same treatment as that of Example 1 was carried out except that the silica-alumina-coated titania fine particles B given in the step (e) were used instead of the aqueous acid dispersion of the titania fine particles, giving a neutral aqueous dispersion of a silica-alumina-coated titania fine-particle composite (Sample G) as the titania fine-particle composite of the present invention.

In Sample G, the ratio of the titania fine particles in the titania fine-particle composite was 91.0 wt %.

Example 8

The same treatment as that of Example 7 was carried out except that a poly (acrylic acid/maleic acid) (20 g) (from. NIPPON SHOKUBAI CO., LTD., molecular weight: 5000, polymerization degree: ca 50) was used instead of the polyacrylic acid, giving a neutral aqueous dispersion of a silica-alumina-coated titania fine-particle composite (Sample H) as the titania fine-particle composite of the present invention.

In Sample H, the ratio of the titania fine particles in the titania fine-particle composite was 92.0 wt %.

Comparative Example 1

The same treatment as that of Example 1 was carried out except the addition of the polyacrylic acid; as a result, aggregation occurred at the neutral pH region, and the resulting dispersion was, therefore, unstable.

Comparative Example 2

The same treatment as that of Example 1 was carried out except that sodium alginate (20 g) (from Wako Pure Chemical Industries Ltd.) was used instead of the polyacrylic acid, giving a neutral aqueous dispersion of a titania fine-particle composite (Sample In Sample I, the ratio of the titania fine particles in the titania fine-particle composite was 85.0 wt %.

Comparative Example 3

The same treatment as that of Example 1 was carried out except that polyvinyl alcohol (20 g) (from Wako Pure Chemical Industries Ltd., molecular weight: 500, polymerization degree: ca 5) was used instead of the polyacrylic acid, giving a neutral aqueous dispersion of a titania fine-particle composite (Sample J).

In Sample J, the ratio of the titania fine particles in the titania fine-particle composite was 80.0 wt %.

Comparative Example 4

A titanium tetrachloride solution (200 g) (dilute hydrochloric acid solution, 16 to 17% in terms of Ti) and polyacrylic acid (4 g) were dissolved in isopropyl alcohol (300 g) to give a solution A. To the solution A, 6N sodium hydroxide was gradually added under stirring at ambient temperature until the pH of the solution became 6. Then, the suspension was aged for 1 hr at the same temperature. Thereafter, the suspension was filtered at a temperature of 50° C., and then subjected to treatment involving decantation and filtration three times by using water at 50° C., which had been prepared separately, to give a wet cake. The wet cake was repulped in pure water, and then dispersed with ultrasound to give a neutral aqueous dispersion of a titania fine-particle composite (with a solid content concentration of 10% and a pH of 7.5) (Sample K).

In the titania fine-particle composite Sample K, the ratio of the polyacrylic acid to the titania was 0.12 part by weight of polyacrylic acid to 1 part by weight of titania, and the ratio of the titania fine particles in the titania fine-particle composite was 89.3 wt %.

Titania fine-particle composite of Comparative Example 4 corresponds to the titania fine-particle composite described in Patent Literature 8 and produced by simultaneously carrying out oxidation of titanium and combination of the titanium with polyacrylic acid.

<X-ray Powder Diffraction Analysis>

Neutral aqueous dispersions of Samples A to K were each dried at 105° C., and pulverized into measurement powders. Then, X-ray diffraction (XRD) measurement was performed on the measurement powders by using an X-ray diffraction instrument (from Spectris Co. Ltd., Trade Name: PANalytical X'Pert PROMPD). The measurement was performed by using a CuKα ray as an X-ray source at a scanning angle 2θ=5 to 70° under the conditions that the tube voltage is 45 kV and the tube current is 40 mA. From the diffraction chart thus made, the half-value width of the peak of maximum diffraction intensity was determined.

Table 1 shows the results thus obtained; Samples A to J each have a half-value width of 2.0° or less, whereas Sample K has a half-value width of more than 2.0°.

TABLE 1

|  |  | Half-value width (°) | Remark |
|---|---|---|---|
| Sample A | Example 1 | 1.422 | Rutile Type |
| Sample B | Example 2 | 1.410 | Rutile Type |
| Sample C | Example 3 | 1.428 | Rutile Type |
| Sample D | Example 4 | 1.435 | Rutile Type |
| Sample E | Example 5 | 1.452 | Rutile Type |
| Sample F | Example 6 | 0.380 | Rutile Type |
| Sample G | Example 7 | 0.420 | Rutile Type |
| Sample H | Example 8 | 0.395 | Rutile Type |
| Sample I | Comparative Example 2 | 1.528 | Rutile Type |
| Sample J | Comparative Example 3 | 1.640 | Rutile Type |
| Sample K | Comparative Example 4 | 2.280 | Anatase Type |

<TG/DTA>

Thermogravimetry/differential thermal analysis (TG/DTA) was performed on Samples A to K by using the following method.

Neutral aqueous dispersions of Samples A to K were dried at 105° C., and pulverized into measurement powders. Then, the measurement powders were analyzed with a thermogravimetry/differential thermal analysis instrument (from SII Nanotechnology Ltd., Product Code: TG/DTA 3000). The analyses were carried out by using a platinum sample cell under air atmosphere from ambient temperature to 1000° C. at a rate of temperature rise of 10° C./min.

Table 2 shows temperatures at which exothermic peaks appeared in the measurement chart. As compared with the exothermic peak in the mixture of the titania fine particles and each polymer, the titania fine-particle composites of the present invention (Sample A to H) each had an exothermic peak at a lower temperature side. Specifically, in the mixtures of the titania fine particles and the polyacrylic acid, exothermic peaks appeared at 400° C., whereas, in Sample A prepared by the combination, exothermic peaks appeared at 240° C. and 300° C. This indicates that exothermic peaks shifted to the lower temperature side considerably. Further, in the composites of the polyacrylic acid and the titania fine particles coated with silica and aluminium oxide (Samples E and G), the exothermic peaks appeared at 188° C. This also indicates that exothermic peaks shifted to the lower temperature side. On the other hand, in Samples I and J, exothermic peaks appeared at the same temperatures as those in the mixtures of the titania fine particles and the individual polymers. In addition, in Sample K, an exothermic peak appeared at 300° C., but did not appear at 240° C.

The exothermic peaks appeared in TG/DTA represent reductions in the weights of the carboxylic monomers or polymers, or the like, derived from their combustion and pyrolysis. From the fact that the exothermic peaks shifted to the lower temperature side, it can be considered that their pyrolysis proceeded at lower temperatures as compared with the pyrolysis of carboxylic acid monomers or polymers, or the like without combination. It can be surmised that in the titania fine-particle composites of the present invention, the intermolecular interactions of the titania fine particles and the carboxylic acid monomer or polymer, or the like are strong because of the assumption that the titania is involved in such pyrolysis.

TABLE 2

|  |  | Exothermic peak (° C.) |
|---|---|---|
| Sample A | Example 1 | 240 and 300 |
| Sample B | Example 2 | 240 and 300 |
| Sample C | Example 3 | 290 |
| Sample D | Example 4 | 274.5 |
| Sample E | Example 5 | 188 |
| Sample F | Example 6 | 290 |
| Sample G | Example 7 | 188 |
| Sample H | Example 8 | 274.5 |
| Sample I | Comparative Example 2 | 245.6 |
| Sample J | Comparative Example 3 | 305 and 418 |
| Sample K | Comparative Example 4 | 300 |
| Mixture of titania fine particles and polyacrylic acid | | 400 |
| Mixture of titania fine particles and sodium polyacrylate | | 400 |
| Mixture of titania fine particles and polymethacrylic acid | | 404 |
| Mixture of titania fine particles and poly(acrylic acid/maleic acid) | | 420 |
| Mixture of titania fine particles and sodium alginate | | 245.6 |
| Mixture of titania fine particles and poly(vinyl alcohol) | | 305 and 418 |

<FT-IR Spectrum Measurement>

Infrared absorption (FT-IR) spectra derived from Samples A to K were measured by using the following method.

Neutral aqueous dispersions of Samples A to K were dried at 105° C., and pulverized into measuring powders. Thereafter, the powders were shaped into KBr tablets, and then infrared absorption spectra specific to the tablets were measured with a Fourier transform infrared spectrophotometer (from Shimadzu Corp., Product Code: FTIR-8300).

Table 3 shows wave numbers at which peaks attributed to carbonyl groups appeared in the resulting spectra. In the titania fine-particle composites of the present invention (Samples A to H), small absorption peaks appeared at the wave numbers where the previously mentioned peaks appeared when the polyacrylate sodium was used alone, and further absorption peaks formed at the lower wave number side (1535 to 1545 $cm^{-1}$). Specifically, in the case where the polyacrylic acid was used alone, a peak attributed to the carbonyl group appeared at 1716.7 $cm^{-1}$. On the other hand, in the composite of the titania fine particles and the polyacrylic acid (Sample A), a small absorption peak appeared at 1558 $cm^{-1}$ as in the case where sodium polyacrylate as a salt obtained through the neutralization of the polyacrylic acid was used alone. Further, in Sample A, another absorption peak appeared at 1543 $cm^{-1}$. Also in the composite of the titania fine particles and the polyacrylate sodium (Sample B), an absorption peak appeared at 1543 cm$^{-1}$ as well as an absorption peak appeared (at 1558 to 1560 cm$^{-1}$) when the polyacrylate sodium was used alone.

On the other hand, in Sample I, an absorption peak appeared at the same position as that in the case of using the sodium alginate alone, and no new peak appeared. That is, in Sample I, it is surmised that chemical combination of the titania fine particles and the sodium alginate via the carbonyl groups thereof does not occur and the sodium alginate attaches to the titania fine particles by any other mechanism.

In Sample K, an absorption peak appeared only at the same position as that in the case of solely using the sodium polyacrylate as a salt obtained through the neutralization of the polyacrylic acid, and no new peak appeared.

TABLE 3

|  |  | Peak attributed to carbonyl group (cm$^{-1}$) |
|---|---|---|
| Sample A | Example 1 | 1558 and 1543 |
| Sample B | Example 2 | 1558 and 1543 |
| Sample C | Example 3 | 1558 and 1539 |
| Sample D | Example 4 | 1560 and 1541 |
| Sample E | Example 5 | 1558 and 1541 |
| Sample F | Example 6 | 1558 and 1539 |
| Sample G | Example 7 | 1558 and 1541 |
| Sample H | Example 8 | 1560 and 1541 |
| Sample I | Comparative Example 2 | 1740 |
| Sample J | Comparative Example 3 | No carbonyl group |
| Sample K | Comparative Example 4 | 1558 |
| Polyacrylic acid |  | 1716.7 |
| Sodium polyacrylate |  | 1558 to 1560 |
| Polymethacrylic acid |  | 1716 |
| Poly(acrylic acid/maleic acid) |  | 1710 |
| Sodium alginate |  | 1740 |
| Polyvinyl alcohol |  | No carbonyl group |

<Aqueous Dispersion Viscosity Measurement>

The viscosity of each of aqueous dispersions of the titanium fine-particle composites was measured by using the following method.

After each of neutral aqueous dispersions of Samples A to J had been prepared (solid content: 25 wt %), the viscosity was measured with a single-cylinder rotational viscometer (from Shibaura Systems Co., Ltd., Trade Name: Vismetron VA-A1). The viscosity measurement was performed at room temperature (25° C.) by using a #3 rotor at a rotational speed of 60 times/min. In Sample K, it was impossible to prepare an aqueous dispersion with a solid content of 25 wt %.

Table 4 shows the results thus obtained. The aqueous dispersions of the titania fine-particle composites of the present invention (Samples A to H) were in the form of a smooth solution. Whereas a typical cream foundation has viscosity of about 20,000 cpz, Samples A to H each have an extremely low viscosity. The viscosity of Sample I and J was higher in order by 1 to 2 degrees as compared with Samples A to H. It should be noted that Sample K was poor in fluidity, at a concentration of 13.5 wt % or higher, to the extent that the rotor could not rotate, and thus its viscosity could not be measured.

From this fact, it is clear that the titania fine-particle composites of the present invention disperse uniformly in the neutral aqueous dispersions, and the aggregation of the titania fine particles does not occur easily.

TABLE 4

|  |  | Viscosity (cpz) |
|---|---|---|
| Sample A | Example 1 | 34 |
| Sample B | Example 2 | 35 |
| Sample C | Example 3 | 200 |
| Sample D | Example 4 | 38 |
| Sample E | Example 5 | 40 |
| Sample F | Example 6 | 210 |
| Sample G | Example 7 | 45 |
| Sample H | Example 8 | 43 |
| Sample I | Comparative Example 2 | 2700 |
| Sample J | Comparative Example 3 | 1500 |
| Sample K | Comparative Example 4 | Unmeasurable |

<Transmission Factors and Ultraviolet Shielding Abilities at Visible Region>

Transmission factors and ultraviolet shielding abilities at the visible region of Samples A to K were evaluated by using the following method.

The neutral aqueous dispersions of Samples A to K were each diluted with pure water so as to have a concentration of 0.0050 wt %. Then, the dispersions were poured into a 10-mm-thick quartz cell, and transmission spectra from the dispersions were measured using a spectrophotometer (from Hitachi Ltd., Product Code:U-300) equipped with an integrating sphere in the range of 280 nm to 450 nm. Transmission factors at 310 nm and 450 nm were determined from the obtained spectra, and the differences between the factors were also calculated.

Table 5 shows the results thus obtained. Samples A to H were equal to or higher than Samples I to K in the shielding ability at the wavelength of 310 nm in the ultraviolet region, and superior in the transmission factor at the wavelength of 450 nm in the visible region.

TABLE 5

|  |  | Transmission factor (%) | | % T at 450 nm-% T |
|---|---|---|---|---|
| Wavelength (nm) |  | 450 | 310 | at 310 nm |
| Sample A | Example 1 | 90.2 | 0.3 | 89.9 |
| Sample B | Example 2 | 88.8 | 0.4 | 88.4 |
| Sample C | Example 3 | 82.5 | 0.2 | 82.3 |
| Sample D | Example 4 | 84.4 | 0.5 | 83.9 |
| Sample E | Example 5 | 80.8 | 1.1 | 79.7 |
| Sample F | Example 6 | 81.5 | 1.2 | 80.3 |
| Sample G | Example 7 | 80.5 | 1.0 | 79.5 |
| Sample H | Example 8 | 80.8 | 1.6 | 79.2 |
| Sample I | Comparative Example 2 | 72.3 | 1.5 | 70.8 |
| Sample J | Comparative Example 3 | 69.9 | 1.2 | 68.7 |
| Sample K | Comparative Example 4 | 92.4 | 46.8 | 45.6 |

<Preparation of Ultraviolet Protection Cosmetics (in Form of Two-layer Dispersion Lotion)>

Ultraviolet protection cosmetics (in the form of a two-layer dispersion lotion) 1 and 2 as skin-care external preparations of the present invention were prepared by using the titania fine-particle composites A and C in accordance with the prescriptions shown in Table 6 below. Ultraviolet protection cosmetics 3 and 4 other than the skin-care external preparations of the present invention were also prepared by using the titania fine-particle dispersions I and J in accordance with the prescriptions shown in Table 6 below. That is, components represented as the group (i) were stirred under heating at 80° C. to give solutions, then components represented as the group (ii) were dispersed into the solutions to give ultraviolet protection cosmetics 1 to 4.

In the ultraviolet protection cosmetic 4, the titania particles sedimented, and it became difficult to redisperse the sedimented titania particles. This can be because the addition of the components other than the dispersion J caused the dissociation of the polyvinyl alcohol, which had a role to disperse the titania fine particles into the system, from the titania particles, resulting in the aggregation and sedimentation of the titania fine particles.

TABLE 7

|  | SPF |
|---|---|
| Ultraviolet protection cosmetic 1 | 25.1 |
| Ultraviolet protection cosmetic 2 | 23.1 |
| Ultraviolet protection cosmetic 3 | 18.4 |

TABLE 6

|  | Components (wt %) | Ultraviolet protection cosmetic 1 | Ultraviolet protection cosmetic 2 | Ultraviolet protection cosmetic 3 | Ultraviolet protection cosmetic 4 |
|---|---|---|---|---|---|
| (i) | 1,1-pentanediol | 2 | 2 | 2 | 2 |
|  | 1,2-pentanediol | 2 | 2 | 2 | 2 |
|  | 1,3-butanediol | 5 | 5 | 5 | 5 |
|  | Ethanol | 5 | 5 | 5 | 5 |
|  | Phenoxyethanol | 0.2 | 0.2 | 0.2 | 0.2 |
|  | POE (20) behenyl alcohol | 0.5 | 0.5 | 0.5 | 0.5 |
|  | Carboxymethylcellulose | 0.1 | 0.1 | 0.1 | 0.1 |
|  | Water | 65.2 | 65.2 | 65.2 | 65.2 |
| (ii) | Titania fine-particle composite A | 20 |  |  |  |
|  | Titania fine-particle composite C |  | 20 |  |  |
|  | Titania fine-particle dispersion I |  |  | 20 |  |
|  | Titania fine-particle dispersion J |  |  |  | 20 |
|  | Total | 100 | 100 | 100 | 100 |

<Measurement of SPF (Sun Protection Factor)>

The SPFs (sun protection factor) of the ultraviolet protection cosmetics 1 to 3 applied to the back of a panelist were measured in accordance with the code of the Japan Cosmetic Industry Association.

Table 7 shows the results thus obtained. The SPFs of the ultraviolet protection cosmetics 1 and 2 are greater than the SPF presented by the ultraviolet protection cosmetic 3, and thus it has been confirmed that a great ultraviolet protective effect can be obtained by using the composite of the present invention as a component of cosmetics. Further, the solid content of the ultraviolet protection cosmetic 3 was separated from the solution and sedimented three days after the preparation. Also, the solid content of the ultraviolet protection cosmetic 4 was separated therefrom and sedimented five days after the preparation. In the ultraviolet protection cosmetics 3 and 4, it can be considered that the fine titanium oxide particles were low in dispersion stability, and therefore aggregated and sedimented.

<Preparation of Ultraviolet Protection Cosmetics (in Form of Water-in-oil Type Preparation)>

Ultraviolet protection cosmetics (in the form of a water-in-oil type preparation) as skin-care external preparations were prepared by using the titania fine-particle composites B and G, the titania fine-particle dispersions I and J in accordance with the prescriptions shown in Table 8. That is, predetermined quantities of components represented as groups (i) and (ii) were each measured out, and after a certain period of time, the group (ii) components were heated to 80° C., and then gradually added to the group (i) components, which were pre-heated to 80° C., under stirring to give emulsions. The emulsions were then cooled under stirring to give ultraviolet protection cosmetics 5 to 8.

The ultraviolet protection cosmetics 5 and 6 containing the titania fine-particle composites B and G were soft to the touch, and provided a refreshing tactile sensation, whereas the ultraviolet protection cosmetic 7 containing the titania fine-particle composite I was heavy to the touch due to the use of the sodium alginate. That is, the ultraviolet protection cosmetics of the present invention were far superior in application characteristics.

TABLE 8

| Component (wt %) | | Ultraviolet protection cosmetic 5 | Ultraviolet protection cosmetic 6 | Ultraviolet protection cosmetic 7 | Ultraviolet protection cosmetic 8 |
|---|---|---|---|---|---|
| (i) | Decamethylsiloxypentasiloxane | 33.5 | 33.5 | 33.5 | 33.5 |
| | Dimethylstearyl ammonium hectorite | 0.05 | 0.05 | 0.05 | 0.05 |
| | Dimethicone | 2 | 2 | 2 | 2 |
| | Sorbitan sesquilaurate | 0.25 | 0.25 | 0.25 | 0.25 |
| | Polyether-modified methylpolysiloxane (from Shin-Etsu Chemical Co., Ltd., "Silicone KF6017") | 0.25 | 0.25 | 0.25 | 0.25 |
| (ii) | Titania fine-particle composite B | 20 | | | |
| | Titania fine-particle composite G | | 20 | | |
| | Titania fine-particle dispersion I | | | 20 | |
| | Titania fine-particle dispersion J | | | | 20 |
| | Water | 32.9 | 32.9 | 32.9 | 32.9 |
| | Glycerin | 1 | 1 | 1 | 1 |
| | 1,3-butanediol | 10 | 10 | 10 | 10 |
| | Potassium glycyrrhizinate | 0.05 | 0.05 | 0.05 | 0.05 |
| | Total | 100 | 100 | 100 | 100 |

<Measurement of SPF (Sun Protection Factor)>

The SPFs (sun protection factor) of the ultraviolet protection cosmetics 5 to 8 applied to the back of a panelist were measured in accordance with the code of the Japan Cosmetic Industry Association.

Table 9 shows the results thus obtained. The SPFs of the ultraviolet protection cosmetics 5 and 6 are greater than the SPFs of the ultraviolet protection cosmetics 7 and 8, and thus it has been confirmed that a great ultraviolet protective effect can be obtained by using the composite of the present invention as a component of cosmetics. Further, the solid content of the ultraviolet protection cosmetic 7 was separated from the solution and sedimented three days after the preparation. Also, the solid content of the ultraviolet protection cosmetic 8 was separated therefrom and sedimented five days after the preparation. In the ultraviolet protection cosmetics 7 and 8, it can be considered that the fine titanium oxide particles were low in dispersion stability, and therefore aggregated and sedimented.

It can be considered that such great ultraviolet protective effect is obtained because the titania fine-particle composite disperses uniformly in the cosmetic, the surface areas of the titania fine particles absorbing ultraviolet increases, and because the crystallinity index of the titania fine particles used as the cores is high, resulting in a great ultraviolet absorbing effect.

TABLE 9

| | SPF |
|---|---|
| Ultraviolet protection cosmetic 5 | 26.1 |
| Ultraviolet protection cosmetic 6 | 23.2 |
| Ultraviolet protection cosmetic 7 | 16.2 |
| Ultraviolet protection cosmetic 8 | 14.1 |

Industrial Applicability

The present invention is applied suitably to skin-care external preparations such as cosmetics.

What is claimed is:

1. An external preparation for skin, comprising a titania fine-particle composite,
wherein the titania fine-particle composite comprises titania fine particles combined with one or more selected from polymers containing, as constituent monomers, a carboxylic acid and/or a carboxylic acid derivative represented by the following general formula (1):

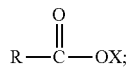

and
wherein, in X-ray powder diffraction analysis of the titania fine-particle composite, a half-value width of a peak of maximum diffraction intensity attributed to titania crystals is 2.0° or less;
wherein a concentration of the titania fine particles in the titania fine-particle composite is in a range of 85 to 99 wt %; and
wherein a maximum diameter of the titania fine particles is 0.001 to 0.1 μm.

2. The external preparation for skin according to claim 1, wherein a content of the titania fine particles is 1.0 to 30 wt %.

3. The external preparation for skin according to claim 1, further comprising 1,3-butanediol.

* * * * *